United States Patent [19]  [11] 4,087,418
Wittle  [45] May 2, 1978

[54] HEXAPEPTIDES AND METHODS FOR THEIR PRODUCTION

[75] Inventor: Eugene Leroy Wittle, Ann Arbor, Mich.

[73] Assignee: Parke, Davis & Company, Detroit, Mich.

[21] Appl. No.: 723,425

[22] Filed: Sep. 15, 1976

[51] Int. Cl.$^2$ .................... C07C 103/52; A61K 37/00
[52] U.S. Cl. .................. 260/112.5 LH; 260/112.5 R; 424/177
[58] Field of Search ............. 260/112.5 R, 112.5 LH; 424/177

[56] References Cited
PUBLICATIONS

Gross, "The Peptides", vol. 2, 1966, Acad. Press., pp. 182, and 232–233.

*Primary Examiner*—Delbert R. Phillips
*Attorney, Agent, or Firm*—Stephen Raines; Frank S. Chow; David B. Ehrlinger

[57] ABSTRACT

New hexapeptides having the formula X-Ser(benzyl)-Tyr(benzyl)-Ala-Leu-Arg-Pro-Y wherein X is t-butoxycarbonyl or benzyloxycarbonyl and Y is lower alkoxy, amino, lower alkylamino or di(lower alkyl)amino.

3 Claims, No Drawings

HEXAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected hexapeptides that are represented by the formula

X-Ser(benzyl)-Tyr(benzyl)-Ala-Leu-Arg-Pro-Y          I and acid addition salts thereof wherein X is t-butoxycarbonyl or benzyloxycarbonyl and Y is lower alkoxy, amino, lower alkylamino or di(lower alkyl)amino.

The preferred compounds of formula I are those wherein X is t-butoxycarbonyl and Y is methoxy or ethylamino.

In formula I, the conventional symbols for amino acid residues of peptide compounds linked thereto are used and each is intended to have the following meaning: Pro, D-prolyl or L-prolyl; Ala, D-alanyl or L-alanyl; Tyr(benzyl), D-tyrosyl(benzyl) or L-tyrosyl(benzyl), Ser(benzyl), D-seryl(benzyl) or L-seryl(benzyl); Leu, D-leucine or L-leucine and Arg, D-arginine or L-arginine. In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. These symbols and terms will alos be used in the formulae that follow for other compounds and each such symbol or term should be understood to have the meaning given above.

Compounds of this invention may be produced by reacting an azide, represented by the formula X-Ser(benzyl)-Tyr(benzyl)-Ala-Leu-N$_3$          II with a compound of the formula Arg-Pro-Y          III in a non-reactive solvent medium, preferably dimethylformamide or a dimethylformamide-tetrahydrofuran mixture wherein X and Y are as previously defined in formula I.

The azide of the formula II is prepared and used in situ, while the compound of formula III is used with the Arg group in the form of an acid-addition salt of a strong acid, such as the hydrochloride or trifluoroacetate. The two components, II and III are generally reacted in approximately equimolar amounts at temperatures of from about −30° C. to about 30° C. for from 16 to 50 hours, although temperatures of from 30° C to 50° C. may be used with a shortened reaction period.

The compounds of formula I are preferably isolated in the form of an acid-addition salt but may if desired be isolated in the form of a free base.

The peptide azide compounds of the formula II that are used as a reactant in the foregoing process are normally prepared in situ by reacting a peptide hydrazide compound represented by the formula

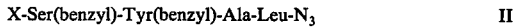

X-Ser(benzyl)-Tyr(benzyl)-Ala-Leu-NHNH$_2$          IV

wherein X is as previously described in formula I with a lower alkyl nitrite, preferably isoamyl nitrite in the presence of an acid in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula IV. The preparation of the azide is carried out at a temperature between −60° and −10° C. Following the in situ formation of the azide of formula II and prior to the further reaction of the peptide azide with the compound of formula III to form the hexapeptide product I, a tertiary amine such as triethylamine is added to the reaction mixture to neutralize the acid used.

The peptide hydrazide compounds of formula IV wherein X is as previously described is prepared by reacting an ester of the formula

X-Ser(benzyl)-Tyr(benzyl)-Ala-Leu-OR$^4$          V wherein R$_4$ is lower alkyl, preferably methyl, with excess hydrazine (1:1.1 to 100) preferably in the form of its hydrate, in an organic solvent, such as dimethylformamide, methanol, ethanol, etc. The reaction is generally carried out at room temperature, although temperatures of from 5° C. to 100° C. may be employed for periods of from about 30 minutes to about 200 hours, preferably about 72 hours.

The compounds of formula V are prepared as shown in the specific examples.

The compounds of formula III are prepared by the following process.

A compound of the formula

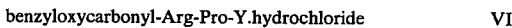

benzyloxycarbonyl-Arg-Pro-Y.hydrochloride          VI is reduced using palladium-on-charcoal and hydrogen in methanol. The reaction is conducted at room temperature for about 3 hours.

The compounds of the formula VI are prepared by reacting N$^\alpha$-benzyloxycarbonyl arginine and proline lower alkyl ester hydrochloride in the presence of 1-hydroxybenztriazole and dicyclohexylcarbodiimide using dimethylformamide as the solvent. The reaction is initially conducted at 0° C. for several hours followed by sixteen hours at room temperature. Where Y is amino, lower alkylamino or di(lower alkyl)amino, the above formed compound is reacted with a large excess of ammonia, a lower alkylamine or a di(lower alkyl)amine in methanol for about 8 days at from room temperature to 45° C.

The compounds of this invention form acid-addition salts with any of a variety of inorganic and organic acids. Pharmaceutically-acceptable acid-addition salts are formed with such acids as hydrochloric, hydrobromic, sulfuric, phosphoric, acetic, succinic, citric, maleic, malic, gluconic, pamoic and related acids. The invention includes acid-addition salts generally as any toxic salt can be converted to the free base or to a pharmaceutically-acceptable salt. The free base and the acid-addition salt forms are interconvertible by adjustment of the pH or by the use of ion-exchange resins. They may differ in solubility properties but except as noted above are otherwise equivalent for purposes of the invention.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Hexapeptides of this invention were screened for LRF antagonist activity in vitro using rat anterior pituitary cell cultures as described by Vale et. al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on the preferred compound.

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| $N^\alpha$-t-tButoxycarbonyl-O-benzyl-L-seryl-O-benzyl-L-tyrosyl-D-alanyl-L-leucyl-L-arginyl-L-proline N-ethylamide | $1 \times 10^{-6}$ | 12.34 | 81 |
| LRF Control | $2.5 \times 10^{-10}$ | 38.98 | |
| Saline Control | | 6.25 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511-512. Thus, the hexapeptides of this invention are useful in controlling ovulation and in restricting fertility.

The invention is illustrated by the following examples.

EXAMPLE 1

$N^\alpha$-t-Butoxycarbonyl-O-benzyl-L-seryl-O-benzyl-L-tyrosyl-D-alanyl-L-leucyl-L-arginyl-L-proline N-ethylamide, hydrochloride $N^\alpha$-t-Butoxycarbonyl-O-benzyl-L-seryl-O-benzyl-L-tyrosyl-D-alanyl-L-leucyl hydrazide, 763 mg. (1 mmol) is converted to the azide by dissolving in 30 ml. of dimethylformamide, cooling to −50° C., and treating with 4.1 ml. (6 mmol) of 1.46N hydrogen chloride in tetrahydrofuran and then with 0.16 ml. (1 mmol) of isopentylnitrite. After 4 hours at about −20° to −40° C., the mixture is treated at −30° C. with one mmol of L-arginyl-L-proline N-ethylamide hydrochloride (derived from the reduction of $N^\alpha$-benzyloxycarbonyl-L-arginyl-L-proline N-ethylamide hydrochloride, 480 mg., with hydrogen and 20% palladium-on-carbon in methanol) dissolved in 10 ml. of dimethylformamide and with 0.84 ml. (6 mmol) of triethylamine. The reaction is stirred at 0° C. to −15° C. for 2 hours, allowed to gradually warm overnight to room temperature and then allowed to stand at room temperature for an additional 7 days.

The reaction mixture is evaporated to dryness at 50° C. and at reduced pressure. The residue is soluble in 5 to 10 ml. of methanol and precipitates on addition of 300 ml. of ether. The white solid is re-precipitated from methanol with ether and then from methanol with ethyl acetate. The product is then crystallized from methanol-ethyl acetate and ether. The product is further purified by chromatography on silica gel with ether-chloroform (1:1); 710 mg. with one methanol of solvation; (liquifies) 135°-143° C.

$N^\alpha$-t-Butoxycarbonyl-O-benzyl-L-seryl-O-benzyl-L-tyrosyl-D-alanyl-L-leucyl hydrazide is obtained from the corresponding methyl ester, 2.28 g., using 2.2 ml. of hydrazine hydrate with 4 ml. of dimethylformamide and 6 ml. of methanol at 25° C. for 3 days. The product is isolated by filtration and washing with methanol; 1.25 g. with ½ a mole of methanol of solvation; m.p. 160°-162° C.

$N^\alpha$-t-Butoxycarbonyl-O-benzyl-L-seryl-O-benzyl-L-tyrosyl-D-alanyl-L-leucine methyl ester is prepared by deprotecting 11.4 g. (20 mmol) of $N^\alpha$-t-butoxycarbonyl-O-benzyl-L-tyrosyl-D-alanyl-L-leucine methyl ester with 50 ml. of trifluoroacetic acid in 40 ml. of dichloromethane at 20° C. for 12 minutes. The mixture is evaporated to dryness at 40° C. under reduced pressure and the residue twice taken into dichloromethane and evaporated to dryness followed by drying under high vacuum for 2 hours. The oily product is dissolved in 70 ml. of dimethylformamide and treated at 10° C. with 10 ml. of triethylamine so that a pH of 7 is obtained. Additional triethylamine, 2.8 ml. (20 mmol) is added, followed by 6 g. (20 mmol) of $N^\alpha$-t-butoxycarbonyl-O-benzyl-L-serine, 2.7 g (20 mmol) of 1-hydroxybenztriazole and (at −5° C.) 4.4. g. of dicyclohexylcarbodiimide. The mixture is slowly stirred to room temperature for two days. The mixture is filtered and the filtrate evaporated at 50° C. under reduced pressure. The residue is dissolved in dichloromethane and filtered. The solution is evaporated to yield an oil which crystallizes from dichloromethane and ether; 10.7 g.; m.p. 67°-71° C.

$N^\alpha$-t-Butoxycarbonyl-O-benzyl-L-tyrosyl-D-alanyl-L-leucine methyl ester is prepared by de-protecting 11.7 g. (33.2 mmol) of $N^\alpha$-benzyloxycarbonyl-D-alanyl-L-leucine methyl ester by reduction using 1 g. of 20% palladium-on-carbon catalyst with hydrogen in 100 ml. of methanol for 3 hours. The solution is filtered and 12.3 g. of $N^\alpha$-t-butoxycarbonyl-O-benzyl-L-tyrosine is added to the filtrate and dissolved. The filtrate is then evaporated and dried under vacuum, and this material is reacted with 4.5 g. of 1-hydroxybenztriazole and 7 g. of dicyclohexylcarbodiimide in 100 ml. of dimethylformamide at −10° C. initially and then allowed to rise to room temperature. The reaction is let stand at room temperature for several days, then filtered and the filtrate evaporated at 50° C. under reduced pressure. The residue is solidified in anhydrous ether, filtered and washed with ether; 12 g.; m.p. 128°-130° C.

$N^\alpha$-Benzyloxycarbonyl-D-alanyl-L-leucine, methyl ester is prepared by the following procedure. A solution of 8.92 g. of $N^\alpha$-benzyloxycarbonyl-D-alanine, 7.28 g. of leucine methyl ester hydrochloride and 5.4 g. of 1-hydroxybenztriazole in 120 ml. of dimethylformamide is cooled to −10° C. with stirring and is treated with 5.6 ml. of triethylamine. The mixture is stirred for ten minutes at −10° C. and is treated with 8.6 g. of dicyclohexylcarbodiimide. The reaction is then stirred at −10° C. for fifteen minutes, brought to 0° C. and stirred to 10° during two hours following which it is stirred overnight at 20° C. The mixture is warmed to 50° C. and stirred for 2 hours.

The reaction mixture is filtered, washing with 20 ml. of dimethylformamide. The solvent is then removed under reduced pressure at 40° C. to leave a thick oil. The oil is dissolved in 400 ml. of ethyl acetate and washed with four 25 ml. portions of 5% sodium bicarbonate solution; twice with dilute hydrochloric acid (1N); twice with saturated sodium chloride solution and the solution dried over anhydrous magnesium sulfate, filtered and evaporated at 40° C. under reduced pressure to a crystalline solid. The solid is covered with 40 ml. of petroleum ether, 10 ml. of ethyl ether added and the solid broken up and filtered. The product melts at 67°–70° C.

$N^\alpha$-Benzyloxycarbonyl-D-alanine is prepared in the following manner. To a solution of 12.5 g. of D-alanine in 70 ml. of 2N sodium hydroxide, with ice cooling and stirring, is added in simultaneous dropwise addition 24 g. of benzyloxycarbonyl chloride and 35 ml. of 4N sodium hydroxide. The pH is maintained at 10 to 12 using a pH electrode in the reaction vessel. The reaction is stirred for one hour further at 4° C. and then extracted with 100 ml. of ethyl ether and acidified to pH 3 with concentrated hydrochloric acid. The product precipitates and is separated by filtration and dried in air; 23.5 g., m.p. 82°–85° C.; $[\alpha]_D^{25} + 14.8°$ (c. 1, 1N acetic acid). A second crop can be obtained from the filtrate by concentration and cooling.

L-Arginyl-L-prolyl-N-ethylamide, hydrochloride is prepared by the following procedure. A solution of 8.7 g. of $N^\alpha$-benzyloxycarbonyl-L-arginyl-L-prolyl-N-ethylamide hydrochloride in 100 ml. of methanol is stirred with 500 mg. of 20% palladium-on-carbon under one inch water pressure of hydrogen for three hours. The catalyst is removed by filtration and the filtrate evaporated under reduced pressure and at 35°–40° C. The residual foam is used without further purification.

$N^\alpha$-Benzyloxycarbonyl-L-arginyl-L-prolyl-N-ethylamide, hydrochloride is prepared according to the following method. To a cold solution of 9.7 g. ethylamine in 50 ml. of methanol is added 2 g. of $N^\alpha$-benzyloxycarbonyl-L-arginyl-L-proline, methyl ester, hydrochloride. The reaction is let stand in a sealed pressure bottle at room temperature and then warmed occasionally to 40°–45° C. during 8 days. It is then evaporated to small volume under reduced pressure. The residual solution is dropped into stirred ethyl ether to precipitate a somewhat sticky white solid which is dried under reduced pressure; $[\alpha]_D^{25} -53°$ (c. 1.02, methanol).

$N^\alpha$-Benzyloxycarbonyl-L-arginyl-L-proline, methyl ester, hydrochloride is made by the following route. A mixture of 25 g. of $N^\alpha$-benzyloxycarbonyl-L-arginine, 13.5 g. of L-proline methyl ester hydrochloride and 11 g. of 1-hydroxybenztriazole in 200 ml. of dimethylformamide is dissolved slowly on stirring for one hour. The mixture is cooled to 0° C., treated with 17 g. of dicyclohexylcarbodiimide and stirred for several hours with cooling and then overnight at room temperature. The mixture is then warmed at 30° C. to 50° C. with stirring for 2 hours and allowed to stand overnight at room temperature. The mixture is filtered, rinsing with a little dimethylformamide, and the filtrate evaporated at 40° C. and reduced pressure to an oily residue. The oil is dissolved in a small amount of methanol and added slowly to 500 ml. of ethyl ether with vigorous stirring. The dispersed droplets solidify and are broken up and separated by filtration. The product is further purified by solution in hot methanol and the addition of ethyl acetate to the appearance of cloudiness and then of ether to turbidity. The solution is seeded and swirled to crystallization and cooled to complete the crystallization. The product is separated by filtration and melts at 125°–130° C. Two recrystallizations from methanol-ethyl acetate-ether raise the melting point to 130°–135° C. Recrystallization from chloroform gives material melting at 165°–167° C.

EXAMPLE 2

$N^\alpha$-t-Butoxycarbonyl-O-benzyl-O-benzyl-L-seryl-O-benzyl-L-tyrosyl-D-alanyl-L-leucyl-L-arginyl-L-proline methyl ester, hydrochloride The above named compound is prepared by the process of claim 1 except that the step involving the reaction of ethylamine with $N^\alpha$-benzyloxycarbonyl-L-arginyl-L-proline, methyl ester, hydrochloride is eliminated.

EXAMPLE 3

$N^\alpha$-Benzyloxycarbonyl-O-benzyl-L-seryl-O-benzyl-L-tyrosyl-D-alanyl-L-leucyl-L-arginyl-L-proline N-ethylamide The above named compound is prepared by the process of claim 1 except that $N^\alpha$-benzyloxycarbonyl-O-benzyl-L-serine (20 mmol) is used in place of $N^\alpha$-t-butoxycarbonyl-O-benzyl-L-serine.

I claim:

1. A hexapeptide of the formula t-butoxy-carbonyl-L-Ser(benzyl)-L-Tyr(benzyl)-D-Ala-L-Leu-L-Arg-L-Pro-N-lower alkylamide and acid addition salts thereof.

2. The hexapeptide of claim 1 having the name $N^\alpha$-t-butoxycarbonyl-O-benzyl-L-seryl-O-benzyl-L-tyrosyl-D-alanyl-L-leucyl-L-arginyl-L-proline N-ethylamide and acid addition salts thereof.

3. The hexapeptide of claim 1 having the name $N^\alpha$-t-butoxycarbonyl-O-benzyl-L-seryl-O-benzyl-L-tyrosyl-D-alanyl-L-leucyl-L-arginyl-L-proline N-ethylamide, hydrochloride.

* * * * *